United States Patent [19]

Lachmann et al.

[11] Patent Number: 5,720,278
[45] Date of Patent: Feb. 24, 1998

[54] INVERSE PROPORTIONAL ASSIST VENTILATION APPARATUS

[75] Inventors: Burkhard Lachmann, Oldenburg, Germany; Govinda Rajan, Huizen, Netherlands

[73] Assignee: Siemens Elema AB, Solna, Sweden

[21] Appl. No.: 756,691

[22] Filed: Nov. 26, 1996

[30] Foreign Application Priority Data

Dec. 1, 1995 [SE] Sweden ..................... 9504311

[51] Int. Cl.$^6$ .............. A61M 16/00; A62B 7/04; F16K 31/02; F16K 31/26
[52] U.S. Cl. .............. 128/204.23; 128/204.21; 128/204.26
[58] Field of Search .............. 128/204.21, 204.26, 128/204.23

[56] References Cited

U.S. PATENT DOCUMENTS

| | | | |
|---|---|---|---|
| 3,848,591 | 11/1974 | Smythe et al. | 128/204.23 |
| 4,036,221 | 7/1977 | Hillsman et al. | 128/204.23 |
| 4,141,356 | 2/1979 | Smargiassi | 128/204.23 |
| 4,206,754 | 6/1980 | Cox et al. | 128/204.23 |
| 4,421,113 | 12/1983 | Gedeon et al. | 128/204.23 |
| 4,635,631 | 1/1987 | Izumi | 128/204.23 |
| 5,044,362 | 9/1991 | Younes | 128/204.23 |
| 5,107,830 | 4/1992 | Younes | 128/204.23 |
| 5,390,666 | 2/1995 | Kimm et al. | 128/204.26 |

FOREIGN PATENT DOCUMENTS 0 459 647  12/1991  European Pat. Off. .

OTHER PUBLICATIONS

"Proportional Assist Ventilation, a New Approach to Ventilatory Support," Younes, American Review Respiratory Disease, vol. 145 (1), Jan. 1992, pp. 114–120.

Primary Examiner—Kimberly L. Asher
Attorney, Agent, or Firm—Hill, Steadman & Simpson

[57] ABSTRACT

A breathing apparatus for supplying a supportive inspiration pulse in response to a sensed inhalation effort of a subject connected to the apparatus has a supportive response controlled so that the amplitude of the inspiration pulse displays an inverse relationship to the magnitude of the sensed inhalation effort.

10 Claims, 2 Drawing Sheets

INVERSE PROPORTIONAL ASSIST VENTILATION APPARATUS

BACKGROUND OF THE INVENTION

1. Field of the Invention

The present invention relates to a breathing apparatus for supplying a respiratory gas to a living being, having a delivery unit for supplying inspiration pulses of respiratory gas to the living being, a sensing unit for sensing spontaneous inhalation efforts of the living being and a control unit for controlling the delivery unit so that it generates a supportive inspiration pulse in response to the sensed inhalation effort.

2. Description of the Prior Art

Normally a breathing apparatus can operate in a number of different ventilation modes, such as volume control, pressure control, volume support, pressure support, etc. These ventilation modes normally allow a patient connected to the apparatus to trigger an inspiration and/or expiration. These possibilities are described, for example, in the Operating Manual to Servo Ventilator 300, pages 78–93, AG 0593 3.5, Sweden, 1993.

In an article entitled "Proportional assist ventilation, a new approach to ventilatory support", Younes, American Review Respiratory Disease; 145(1): 114–120, January 1992, a specific variation of the pressure support mode is described. In the described mode, Proportional Assist Ventilation (PAV), the apparatus is controlled so that the pressure delivered at the airway increases in proportion to the patient's instantaneous effort. In other words, the patient's own effort to inhale is amplified. The purpose of the PAV mode is to increase comfort for the patient, reduce peak airway pressure and preserve and enhance the patient's own reflex.

There are, however, some negative effects associated with the PAV mode. One important disadvantage is that this mode may make the patient dependant on the apparatus in the support mode. Other drawbacks (mentioned in the article) are dependence on spontaneous effort, pressure "run-away" and problems with PAV and breathing patterns.

SUMMARY OF THE INVENTION

An object of the present invention is to provide a breathing apparatus operable in an improved ventilation mode.

This object is achieved in a breathing apparatus according to the invention wherein the control unit controls the delivery unit so that it generates a supportive inspiration pulse of respiratory gas, the amplitude of which displays an inverse relationship to the magnitude of the sensed inhalation effort, sensed by the sensing unit.

By having an inverse relationship, which may be linear or non-linear, the supportive response from the apparatus will decrease as the patient's own effort increases. In practice this will provide a patient who has low inspiratory drive to receive a sufficient ventilatory assist, and as the pateint's inspiratory drive increases the support response will decrease so that the patient is induced to activate the respiratory muscles even further.

DESCRIPTION OF THE PREFERRED EMBODIMENTS

Figure 1:
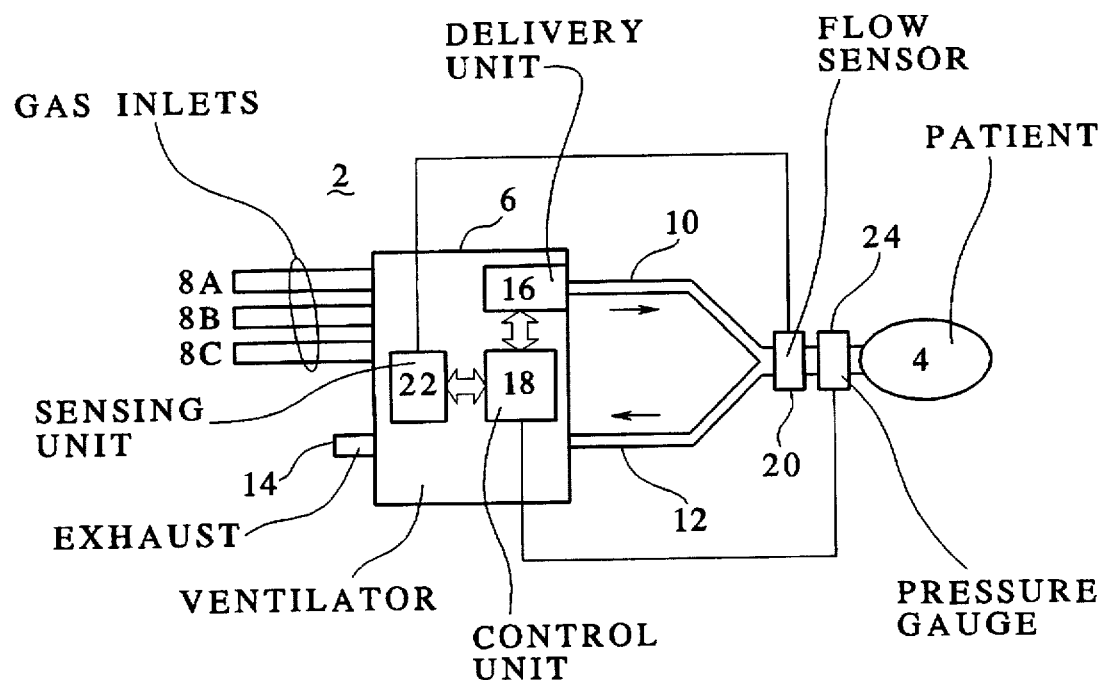
FIG. 1 shows an embodiment of a breathing apparatus according to the invention.

A breathing apparatus 2 according to the invention is shown in FIG. 1. The breathing apparatus 2 is connected to a patient 4 for supplying respiratory gas during inspiration and to remove expired gas during expiration. The breathing apparatus 2 includes a ventilator 6 which can receive the gas components of the respiratory gas via gas inlets 8A, 8B and 8C. The gases could be, for example, compressed air and oxygen. Other gas mixtures are also feasible.

The respiratory gas is delivered to the patient 4 via an inspiration line 10. Exhaled gas is removed from the patient 4 via an expiration line 12, back to the ventilator 6. The exhaled gas is then removed from the ventilator 6 via an exhaust 14 to ambient air or to an evacuation system (not shown). The generation of inspiration pulses is controlled by a delivery unit 16 in the ventilator 6. In response to a control signal from a control unit 18 the delivery unit 16 will generate an inspiration pulse having a defined pressure and/or flow amplitude. The duration of the inspiration pulse may also be controlled by the control unit 18, but it may alternatively be controlled by sensing exhalation efforts from the patient 4.

In order to give a supportive inspiration pulse in response to an inhalation effort from the patient 4, a flow sensor 20 is arranged near the patient 4 in order to sense the inhalation effort of the patient 4. The flow signal from the flow sensor 20 is sent to a sensing unit 22 for determining the magnitude of the inhalation effort. This information is then transferred to the control unit 18 which determines the supportive response to be given in relation to the sensed inhalation effort, whereupon the delivery unit 16 generates the supportive inspiration pulse and delivers it to the patient 4 via the inspiration line 10.

In order to avoid too strong of fluctuations in the supportive response, a running average for the inspiration effort during two or more breaths could be used, instead of the instantaneous inspiration effort in each breath.

Figure 2:
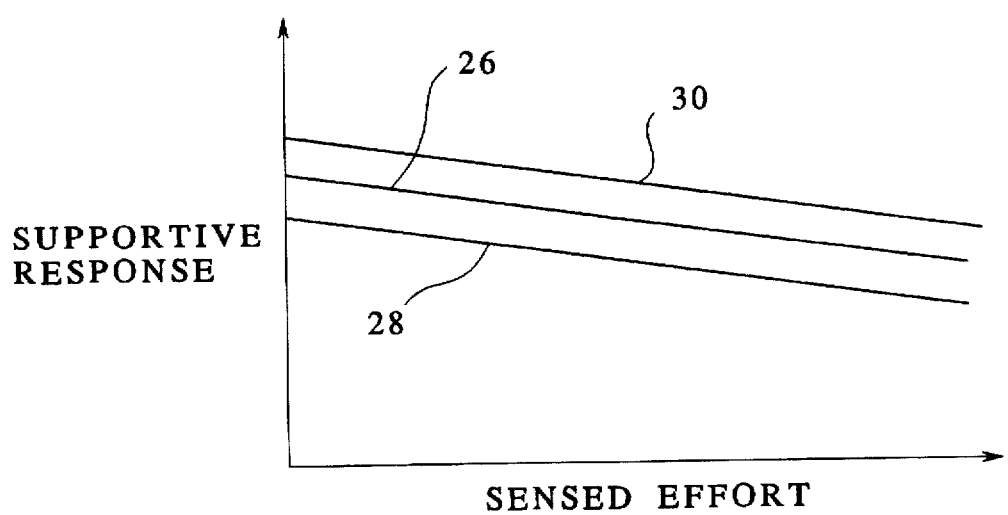
FIG. 2 shows a first relationship between inhalation effort and supportive response which can be used in the apparatus of FIG. 1.

In FIG. 2 the relationship between the sensed effort and the supportive response is shown in a diagram, where the line 26 indicates that the relationship is inverse. The supportive response axis indicates the amplitude of the inspiration pulse, i.e. pressure amplitude in pressure control and pressure support modes, flow amplitude in volume control mode, etc. This means that a low inhalation effort from the patient 4 will result in a relatively higher supportive response from the ventilator than for a high inhalation effort. The higher support for low efforts makes sure that the patient 4 will receive a sufficient amount of respiratory gas. As the condition of the patient 4 improves and a stronger inhalation effort is made the supportive response is decreased. This decrease will cause some extra resistance for the patient 4, thereby forcing the patient 4 to use the respiratory muscles more actively. This respiration training can shorten the recovery time for the patient.

A refinement of this behavior is also achieved with the breathing apparatus 2 (FIG. 1), by arranging a pressure gauge 24 to sense the pressure in or near the mouth of the patient 4. The measured pressure is fed to the control unit 18 which determines the pressure in the mouth of the patient 4 at a predetermined time after the onset of an inspiration, preferably at 0.1 seconds after onset of inspiration. This pressure, usually designated $P_{0.1}$ gives an indication of use by the patient 4 of his or her respiratory muscles. It is also an indicator of the condition of the lungs. If the pressure $P_{0.1}$ increases during a series of inhalations, the lungs may be stiff and the supportive response is thereby decreased, as shown with line 28 in FIG. 2. For a specific sensed effort the supportive response thus will be lessened. This is made in order to avoid too high pressures within the lung, which may damage the lung. If the pressure $P_{0.1}$ decreases over a number of inspiration pulses, however, the supportive response to a specific effort may be increased as shown by the line 30.

Figure 3:
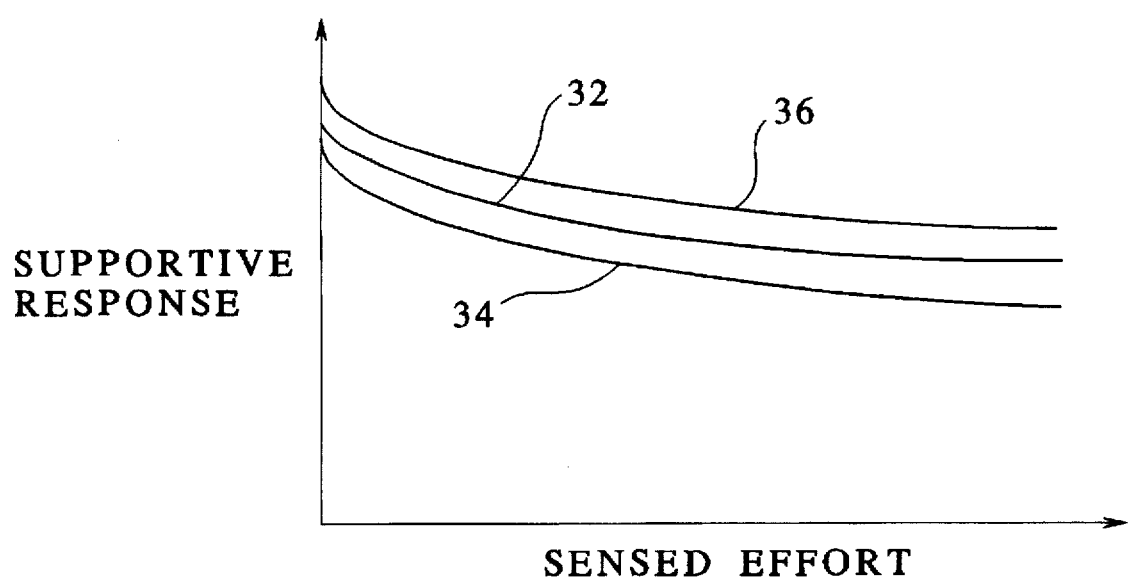
FIG. 3 shows a second relationship between inhalation effort and supportive response which can be used in the apparatus of FIG. 1.

In FIG. 2 the inverse relationship was shown as a linear function, but, as can be seen in FIG. 3, the relationship need not be linear. In FIG. 3 the non-linear lines 32, 34 and 36 correspond in function to the linear lines 26, 28 and 30 respectively in FIG. 2.

Several variations of the above described apparatus can easily be realized by those skilled in the art. For instance, the flow sensor 20 could be replaced by a pressure sensor (or by the pressure gauge 24) for determining the sensed inhalation effort. Also, the inhalation effort can be sensed by sensors within the ventilator and also the pressure in or near the mouth of the patient 4 can be determined by measuring the pressure within the ventilator and calculate the pressure in the mouth of the patient 4.

The inverse proportional assist ventilation here described may be used for all ventilation modes and in particular for the pressure support mode. A continuous basic flow of respiratory gas can be delivered by the ventilator 6 and the supportive inspiration pulses would then be superimposed on this basic flow. Such a continuous basic flow provides an immediate supply of respiratory gas at the onset of every inhalation. This reduces the resistance which the patient needs to overcome in order to receive the respiratory gas. Without the basic flow, the apparatus would have to react instantly at the first sign of inhalation, in order to provide the respiratory gas without delay for the patient. As in other ventilator modes, a security arrangement could be included, in which controlled respiration is provided if the patient cannot obtain a sufficient spontaneous respiration within a specific time.

It is also possible to automatically adjust the support so that the control unit selects the best operation mode for the patient, i.e. control or support mode.

Other parameters, such as the relation between inspiration and expiration times (I:E ratio) and respiratory rate (RR) may also be varied automatically based on the inhalation effort.

Although modifications and changes may be suggested by those skilled in the art, it is the intention of the inventors to embody within the patent warranted hereon all changes and modifications as reasonably and properly come within the scope of their contribution to the art.

We claim as our invention:

1. A breathing apparatus for supplying a respiratory gas to a subject, comprising:

delivery means for supplying respiratory gas to a respirating subject;

sensing means for sensing spontaneous inhalation efforts of said respirating subject; and control means for controlling said delivery means for causing said delivery means to emit a supportive inspiration pulse, in response to a sensed inhalation effort having a magnitude as sensed by said sensing means, and having an amplitude in inverse relationship to said magnitude of said sensed inhalation effort.

2. A breathing apparatus as claimed in claim 1 wherein said delivery means comprises means for supplying a continuous flow of respiratory gas to said respirating subject, and wherein said control means comprises means for superimposing said supportive inspiration pulse on said continuous flow of respiratory gas.

3. A breathing apparatus as claimed in claim 1 wherein said sensing means comprises a flow sensor.

4. A breathing apparatus as claimed in claim 1 wherein said sensing means comprises a pressure sensor.

5. A breathing apparatus as claimed in claim 1 wherein said control means comprises means for calculating a running average of the magnitude of said inhalation effort over at least two breathing cycles of said respirating subject and for controlling the emission of said supportive inspiration pulse by said delivery means based on said running average.

6. A breathing apparatus as claimed in claim 1 wherein said delivery means comprises means for delivering a pressure pulse of said respiratory gas as said supportive inspiration pulse.

7. A breathing apparatus as claimed in claim 1 further comprising pressure gauge means for measuring a pressure of said respiratory gas at said respirating subject, and wherein said control means comprises means for identifying a pressure, as measured by said pressure gauge means, at a predetermined time after an onset of each sensed inhalation effort and for controlling emission of said supportive inspiration pulse by said delivery means dependent both on said magnitude of said sensed inhalation effort and on said pressure at said predetermined time.

8. A breathing apparatus as claimed in claim 7 wherein said control means comprises means for determining a pressure change at each sensed inhalation effort and means for adapting said inverse relationship based on said pressure change.

9. A breathing apparatus as claimed in claim 7 wherein said control means comprises means for identifying said pressure as measured by said pressure gauge at approximately 0.1 seconds after an onset of each sensed inhalation effort.

10. A breathing apparatus as claimed in claim 1 wherein said control means comprises means for causing said delivery means to generate said supportive inspiration pulse with said inverse relationship comprising a linear function.

* * * * *